United States Patent
Lewis

(10) Patent No.: US 8,535,363 B1
(45) Date of Patent: Sep. 17, 2013

(54) FACIAL HEATING PAD DEVICE

(76) Inventor: Falenia Lewis, Glendale, KY (US)

( * ) Notice: Subject to any disclaimer, the term of this patent is extended or adjusted under 35 U.S.C. 154(b) by 293 days.

(21) Appl. No.: 12/913,416

(22) Filed: Oct. 27, 2010

(51) Int. Cl.
*A61F 7/00* (2006.01)
*H05B 3/00* (2006.01)
*H05B 3/54* (2006.01)

(52) U.S. Cl.
USPC .......................... 607/109; 219/211; 219/528

(58) Field of Classification Search
USPC ............ 607/96, 108–112; 219/211, 528–529
See application file for complete search history.

(56) References Cited

U.S. PATENT DOCUMENTS

| | | | |
|---|---|---|---|
| 2,038,275 A * | 4/1936 | Fogg | 219/527 |
| 3,173,419 A | 3/1965 | Dubilier et al. | |
| 3,623,485 A * | 11/1971 | Price | 607/112 |
| 5,169,384 A | 12/1992 | Bosniak et al. | |
| D354,140 S | 1/1995 | Kelly | |
| D396,294 S | 7/1998 | Lahr | |
| 5,800,490 A * | 9/1998 | Patz et al. | 607/108 |
| 6,155,995 A | 12/2000 | Lin | |
| 7,559,907 B2 | 7/2009 | Krempel et al. | |
| 2005/0131504 A1 | 6/2005 | Kim | |
| 2007/0034622 A1* | 2/2007 | Ruminski | 219/528 |
| 2009/0032523 A1* | 2/2009 | Youngblood | 219/528 |

* cited by examiner

*Primary Examiner* — Linda Dvorak
*Assistant Examiner* — Adam Avigan

(57) ABSTRACT

A facial heating pad device provides a dry heating pad producing dry, hot heat and an opposed moist heating pad producing moist warm heat. The device includes a face pad, a power supply operationally coupled to the face pad, and a control unit. The control unit is operationally coupled to the face pad and the power supply for selectively providing power to heat the face pad. The face pad includes a dry heating portion operationally coupled to the control unit for selectively providing dry heat when the dry heating portion is heated by the power supply. The face pad also includes a moist heating portion operationally coupled to the control unit for selectively providing moist heat when the moist heating portion is heated by the power supply.

15 Claims, 3 Drawing Sheets

FACIAL HEATING PAD DEVICE

BACKGROUND OF THE DISCLOSURE

Field of the Disclosure

The disclosure relates to heating pads and more particularly pertains to a new heating pad for providing a dry heating pad producing dry, hot heat and an opposed gel heating pad producing moist warm heat.

SUMMARY OF THE DISCLOSURE

An embodiment of the disclosure meets the needs presented above by generally comprising a face pad, a power supply operationally coupled to the face pad, and a control unit. The control unit is operationally coupled to the face pad and the power supply for selectively providing power to heat the face pad. The face pad includes a dry heating portion operationally coupled to the control unit for selectively providing dry heat when the dry heating portion is heated by the power supply. The face pad also includes a moist heating portion operationally coupled to the control unit for selectively providing moist heat when the moist heating portion is heated by the power supply.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
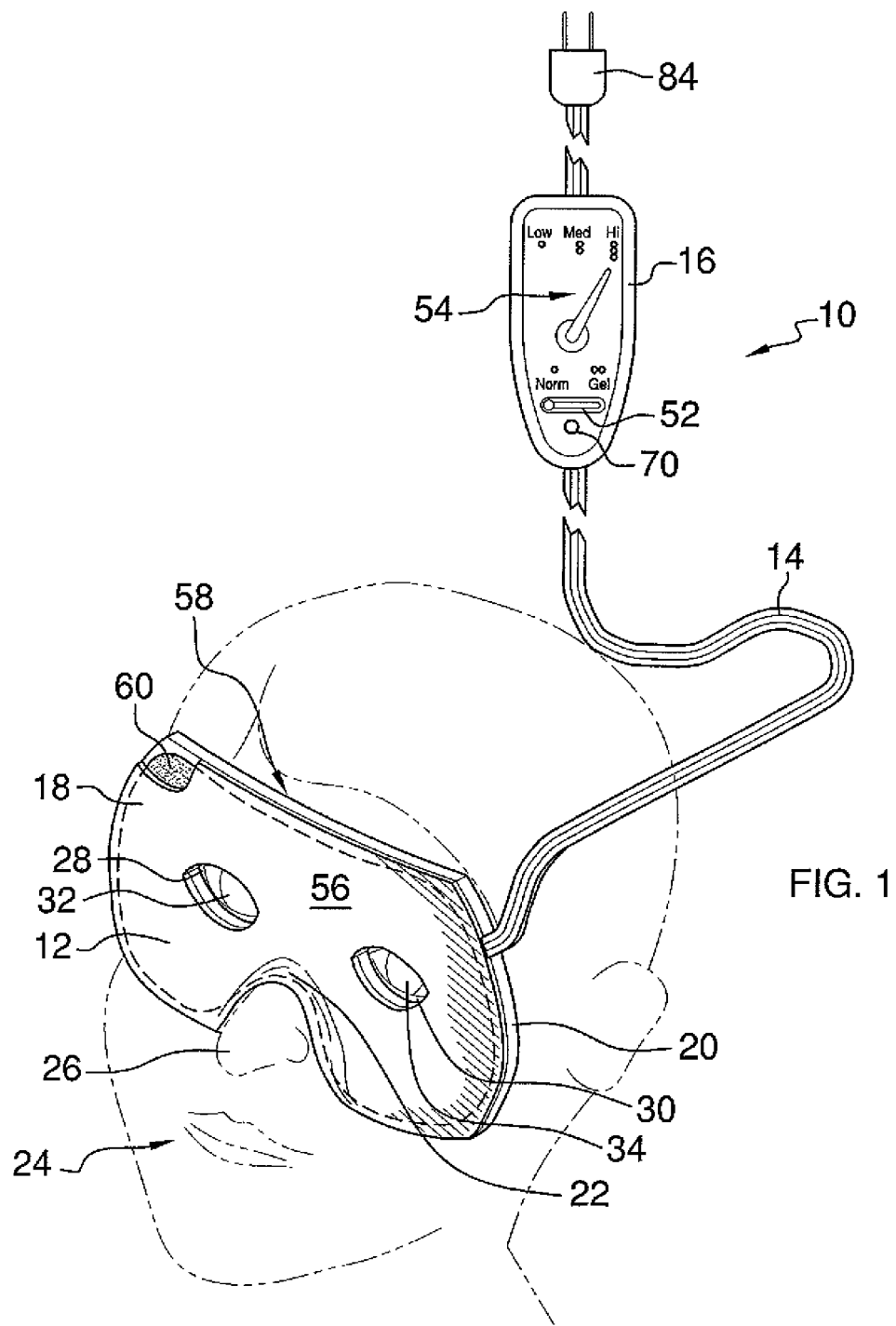
FIG. 1 is a top front side perspective view of a facial heating pad device according to an embodiment of the disclosure.
Figure 2:
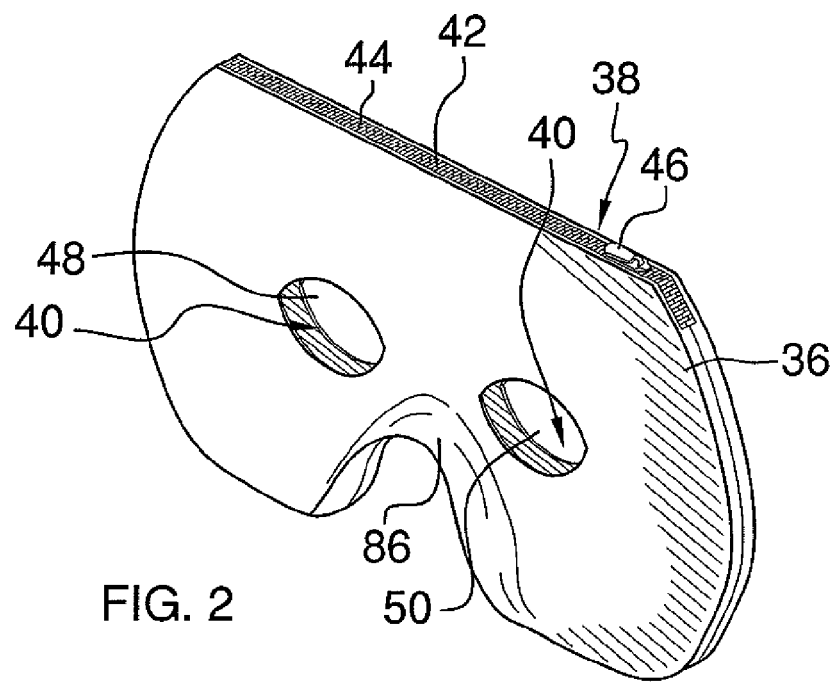
FIG. 2 is a top front side perspective view of a heating pad cover of an embodiment of the disclosure.
Figure 3:
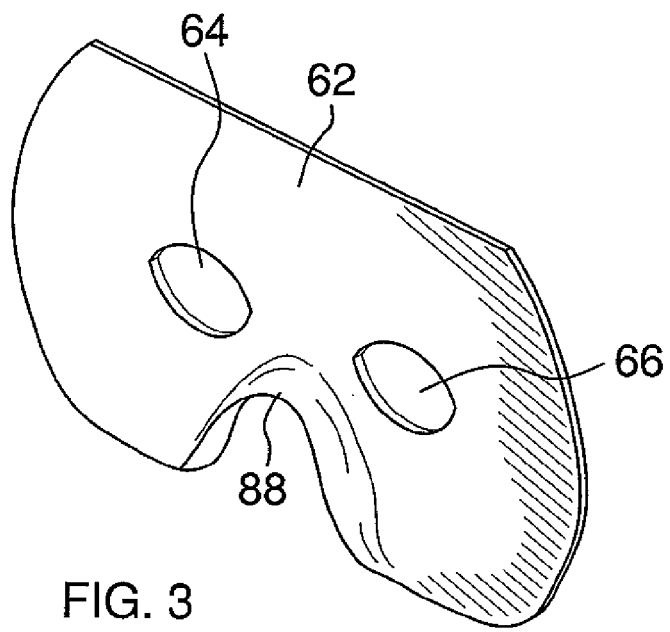
FIG. 3 is a top front side perspective view of a facial cover of an embodiment of the disclosure.
Figure 4:
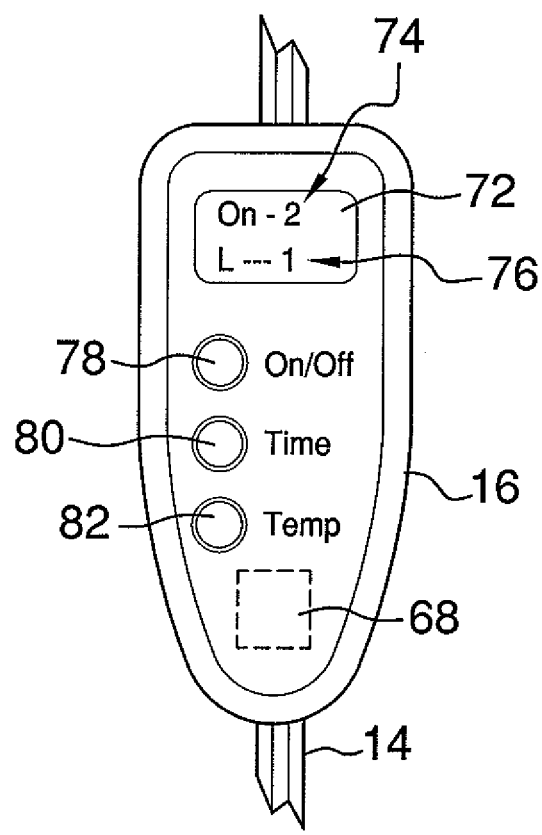
FIG. 4 is a front view of a control unit of an embodiment of the disclosure.

With reference now to the drawings, and in particular to FIGS. 1 through 4 thereof, a new heating pad embodying the principles and concepts of an embodiment of the disclosure and generally designated by the reference numeral 10 will be described.

As best illustrated in FIGS. 1 through 4, the facial heating pad device 10 generally comprises a face pad 12, a power supply 14 operationally coupled to the face pad 12, and a control unit 16 operationally coupled to the face pad 12 and the power supply 14 for selectively providing power to heat the face pad 12. The face pad 12 includes a dry heating portion 18 operationally coupled to the control unit 16 for selectively providing dry heat when the dry heating portion 18 is heated by the power supply 14. The face pad 12 also includes a moist heating portion 20 operationally coupled to the control unit 16 for selectively providing moist heat when the moist heating portion 20 is heated by the power supply 14.

The face pad 12 has a nose arch portion 22 designed for contacting a human face 24 adjacent a nose 26 of the human face 24. The nose arch portion 22 is sufficiently flexible to permit moving the nose arch portion 22 as needed to extend outwardly from the human face 24 in contact with the nose 26 regardless of whether the dry heating portion 18 or the moist heating portion 20 is directed toward the human face 24. The face pad 12 has a pair of eye openings 28,30 designed for positioning over eyes 32,34 of the human face 24 when the face pad 12 is positioned on the human face 24. A face pad cover member 36 has an opening 38 and an interior 40 dimensioned to receive the face pad 12. The face pad cover member 36 includes a closure 42 for selectively closing the opening 38 in the face pad cover member 36. The closure 42 may be a zipper 44 having a zipper head 46 to facilitate manipulation of said zipper 44. The face pad cover member 36 also has a cover member nose arch 86 and a pair of eye apertures 48,50 positioned such that the eye openings 28,30 align with the eye apertures 48,50 when the face pad 12 is positioned in the interior 40 of the face pad cover member 36.

The moist heating portion 20 includes a gel 60 heatable by the power supply 14. Heating of the gel 60 produces warm heat that is suited for heating absorbent material that has been pre-soaked to produce moist heat. The gel 60 is designed to retain heat and is dispersed throughout the full area of the moist heating portion 20. Thus, the gel 60 requires greater power from the power supply 14 in a given amount of time to achieve a similar temperature to the dry heating portion 18, which is constructed in similar fashion to conventionally known heating pads. The gel 60 provides a heavier and more form fitting character than that of the dry heating portion 18 alone. Used in combination with a pre-soaked absorbent material, such as a cover sheet 62, the moist heating portion 20 produces warm moist heat as desired.

The control unit 16 includes an on/off indicator 70 and a switch 52 operationally coupled to the dry heating portion 18 and the moist heating portion 20 for selectively heating one of the dry heating portion 18 and the moist heating portion 20. The switch 52 accommodates for increased power to the moist heating portion 20 due to the incorporation of the gel 60 as described above. The control unit 16 includes a temperature control 54 operationally coupled to the dry heating portion 18 and the moist heating portion 20 for selectively varying an amount of heat produced by the face pad 12.

The dry heating portion 18 and the moist heating portion 20 are positioned on opposite faces 56,58 of the face pad 12. A cover sheet 62 is constructed of an absorbent material to retain moisture when soaked prior to positioning the cover sheet 62 on the human face 24. Thus, the cover sheet 62 provides an outside source of moisture for use with the moist heating portion 20 of the face pad 12. The cover sheet 62 has a sheet nose arch 88 and a pair of eye holes 64,66 designed for positioning over eyes 32,34 of the human face 24 in alignment with the eye openings 28,30 when the face pad 12 is positioned on the human face 24 with the moist heating portion 20 facing the human face 24.

The control unit 16 may also include a timer 68 operationally coupled between the power supply 14 and the face pad 12 for providing heat to the face pad 12 for a selectable duration of time. The control unit 16 may include a liquid crystal diode display screen 72, as shown in the alternate embodiment in FIG. 4. The display screen 72 may have a temperature display indicator 74 and a duration indicator 76. The temperature display indicator 74 may be designed to cycle through heat levels for both the dry heating portion 18 and the moist heating portion 20. The control unit 16 includes an on/off control button 78, a time duration control button 80, and a temperature control button 82 each operationally coupled to the face pad 12, the display screen 72, and the power supply 14 to provide operational control of heat distributed by the face pad 12.

In use, the power supply 14 is plugged into an outlet using plug 84. The face pad 12 is positioned in the face pad cover member 36. The covered face pad 12 is then positioned as desired on the human face 24 covering the cheeks from the eyes 32,34 down to the area of the face covering the eye teeth of the user for full coverage of the sinuses. Either the dry heating portion 18 or the moist heating portion 20 may be positioned facing the human face 24. The cover sheet 62 is moistened and positioned between the face pad 12 and the human face 24 as desired, particularly when the moist heating portion 20 is directed towards the human face. The control unit 16 is manipulated to provide the desired amount of heat for the desired duration of time and in the desired manner using the dry heating portion 18 or the moist heating portion 20.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A facial heating pad device comprising:
a face pad;
a power supply operationally coupled to said face pad;
a control unit operationally coupled to said face pad and said power supply for selectively providing power to heat said face pad;
wherein said face pad includes a dry heating portion operationally coupled to said control unit for selectively providing dry heat when said dry heating portion is heated by said power supply;
wherein said face pad includes a moist heating portion operationally coupled to said control unit for selectively providing moist heat when said moist heating portion is heated by said power supply;
wherein said dry heating portion and said moist heating portion are positioned on opposite faces of said face pad, each of said dry heating portion and said moist heating portion extending continuously across the entirety of each of an associated one of said faces; and
wherein said control unit includes a switch operationally coupled to said dry heating portion and said moist heating portion for selectively heating one of said dry heating portion and said moist heating portion.

2. The facial heating pad device of claim 1, further including said face pad having a nose arch portion adapted for contacting a human face adjacent a nose of the human face.

3. The facial heating pad device of claim 1, further including said face pad having a pair of eye openings adapted for positioning over eyes of a human face when said face pad is positioned on the human face.

4. The facial heating pad device of claim 3, further including a cover sheet having a pair of eye holes, said cover sheet being absorbent for retaining moisture, said eye holes being adapted for positioning over eyes of a user in alignment with said eye openings when said face pad is positioned on the human face with said moist heating portion facing the human face.

5. The facial heating pad device of claim 1, further including a face pad cover member having an opening and an interior dimensioned to receive said face pad.

6. The facial heating pad device of claim 5, wherein said face pad cover member includes a closure for selectively closing said opening in said face pad cover member.

7. The facial heating pad device of claim 5, further including said face pad cover member having a pair of eye apertures, said eye apertures being positioned such that said eye openings align with said eye apertures when said face pad is positioned in said interior of said face pad cover member.

8. The facial heating pad device of claim 1, wherein said control unit includes a temperature control operationally coupled to said dry heating portion and said moist heating portion for selectively varying an amount of heat produced by said face pad.

9. The facial heating pad device of claim 1, wherein said moist heating portion includes a gel heatable by said power supply.

10. The facial heating pad device of claim 1, wherein said control unit includes a timer operationally coupled between said power supply and said face pad for providing heat to the face pad for a selectable duration of time.

11. The facial heating pad device of claim 10, wherein said control unit includes a display screen having a temperature display indicator and a duration indicator.

12. The facial heating pad device of claim 11, wherein said control unit includes an on/off control button, a time duration control button, and a temperature control button operationally coupled to said face pad and said display screen.

13. The facial heating pad device of claim 1, wherein said control unit includes an on/off indicator.

14. A facial heating pad device comprising:
a face pad;
a power supply operationally coupled to said face pad;
a control unit operationally coupled to said face pad and said power supply for selectively providing power to heat said face pad; and
wherein said face pad includes a dry heating portion operationally coupled to said control unit for selectively providing dry heat when said dry heating portion is heated by said power supply;
wherein said face pad includes a moist heating portion operationally coupled to said control unit for selectively providing moist heat when said moist heating portion is heated by said power supply;
said face pad having a nose arch portion adapted for contacting a human face adjacent a nose of the human face;
said face pad having a pair of eye openings adapted for positioning over eyes of a human face when said face pad is positioned on the human face;
a face pad cover member having an opening and an interior dimensioned to receive said face pad;

wherein said face pad cover member includes a closure for selectively closing said opening in said face pad cover member;

said face pad cover member having a pair of eye apertures, said eye apertures being positioned such that said eye openings align with said eye apertures when said face pad is positioned in said interior of said face pad cover member;

wherein said control unit includes a switch operationally coupled to said dry heating portion and said moist heating portion for selectively heating one of said dry heating portion and said moist heating portion;

wherein said control unit includes a temperature control operationally coupled to said dry heating portion and said most moist heating portion for selectively varying an amount of heat produced by said face pad;

wherein said dry heating portion and said moist heating portion are positioned on opposite faces of said face pad, each of said dry heating portion and said moist heating portion extending continuously across the entirety of each of an associated one of said faces;

wherein said moist heating portion includes a gel heatable by said power supply;

an absorbent cover sheet having a pair of eye holes, said eye holes being adapted for positioning over eyes of a user in alignment with said eye openings when said face pad is positioned on the human face with said moist heating portion facing the human face; and wherein said control unit includes an on/off indicator.

15. The facial heating pad device of claim 14, further comprising:

wherein said control unit includes a timer operationally coupled between said power supply and said face pad for providing heat to the face pad for a selectable duration of time;

wherein said control unit includes a display screen having a temperature display indicator and a duration indicator; and wherein said control unit includes an on/off control button, a time duration control button, and a temperature control button operationally coupled to said face pad and said display screen.

* * * * *